(12) United States Patent
Yang

(10) Patent No.: US 8,992,971 B2
(45) Date of Patent: Mar. 31, 2015

(54) NON-ANIMAL SOFT CAPSULE SHELL COMPOSITION HAVING IMPROVED DISINTEGRATION AND SHELL HARDNESS

(75) Inventor: Joo-Hwan Yang, Gyeonggi-do (KR)

(73) Assignee: Suheung Capsule Co., Ltd., Bucheon-si (KR)

( * ) Notice: Subject to any disclaimer, the term of this patent is extended or adjusted under 35 U.S.C. 154(b) by 2 days.

(21) Appl. No.: 13/825,304

(22) PCT Filed: Apr. 18, 2012

(86) PCT No.: PCT/KR2012/002926
§ 371 (c)(1),
(2), (4) Date: Mar. 20, 2013

(87) PCT Pub. No.: WO2012/144789
PCT Pub. Date: Oct. 26, 2012

(65) Prior Publication Data
US 2013/0302309 A1    Nov. 14, 2013

(30) Foreign Application Priority Data

Apr. 20, 2011 (KR) .................. 10-2011-0036823
Mar. 16, 2012 (KR) .................. 10-2012-0026919
Mar. 16, 2012 (KR) .................. 10-2012-0026920

(51) Int. Cl.
*A61K 9/48* (2006.01)
*A61K 47/36* (2006.01)
*A61J 3/07* (2006.01)

(52) U.S. Cl.
CPC ............ *A61K 47/36* (2013.01); *A61K 9/4816* (2013.01); *A61J 3/07* (2013.01)
USPC ...................................................... 424/451

(58) Field of Classification Search
None
See application file for complete search history.

(56) References Cited

U.S. PATENT DOCUMENTS

| 6,214,376 | B1  |   | 4/2001  | Gennadios |
|-----------|-----|---|---------|-----------|
| 6,340,473 | B1  | * | 1/2002  | Tanner et al. ................ 424/451 |
| 6,582,727 | B2  | * | 6/2003  | Tanner et al. ................ 424/451 |
| 2006/0246127 | A1 | * | 11/2006 | Freier ........................... 424/451 |
| 2007/0134493 | A1 | * | 6/2007  | Meghpara ................. 428/402.2 |

FOREIGN PATENT DOCUMENTS

| JP | 2007-153851 A | 6/2007 |
| JP | 2007-524527 A | 8/2007 |
| JP | 2008-519075 A | 6/2008 |
| KR | 10-2002-0082460 A | 10/2002 |
| KR | 10-2010-0047349 A | 5/2010 |
| WO | WO 01/03677 | 1/2001 |
| WO | WO 2004/091530 | 10/2004 |
| WO | WO 2008/117682 | 10/2008 |

OTHER PUBLICATIONS

International Search Report for International Application No. PCT/KR2012/002926, mailed Oct. 31, 2012, 3pages.

* cited by examiner

*Primary Examiner* — Allison Fox
*Assistant Examiner* — Yvonne Pyla
(74) *Attorney, Agent, or Firm* — Sterne, Kessler, Goldstein & Fox P.L.L.C.

(57) ABSTRACT

The present invention relates to a non-animal soft capsule shell composition having improved disintegration stability and shell hardness. More particularly, the present invention relates to a non-animal soft capsule shell composition and to a method for preparing same, in which an antioxidant and a disintegration aid are added to the non-animal soft capsule shell composition that is typically made of starch or a starch derivative, gums, a plasticizer, a buffering agent, and purified water which inhibit starch retrogradation and thus inhibit an increase in disintegration stability and capsule shell hardness, thereby improving disintegration stability and shell hardness.

7 Claims, No Drawings

NON-ANIMAL SOFT CAPSULE SHELL COMPOSITION HAVING IMPROVED DISINTEGRATION AND SHELL HARDNESS

This is a 371 national phase application of PCT/KR2012/002926 filed on Apr. 18, 2012, claiming priorities to Korean Patent Application No. 10-2011-36823 filed on Apr. 20, 2011, Korean Patent Application No. 10-2012-26919 filed on Mar. 16, 2012 and Korean Patent Application No. 10-2012-26920 filed on Mar. 16, 2012, the contents of which are incorporated herein by references.

TECHNICAL FIELD

The present invention relates to a non-animal derived soft capsule shell composition having improved disintegration and shell hardness. More specifically, this invention relates to a non-animal derived soft capsule shell composition comprising i) at least one starch selected from raw starch, acid modified starch, hydroxypropylated modified starch, α-modified starch, cross-linked modified starch, starch hydrozylate and/or mixed starch of raw starch and modified starch; ii) at least one gum selected from arabic gum, tragacanth gum, karaya gum, ghatti gum, guar gum, locust bean gum, tara gum, konjac, algin, agar, carrageenan, pullulan, pectin, gellan, mannan and/or xanthan gum; and iii) plasticizer, buffering agent, antioxidant, disintegration agent and a suitable amount of purified water. Further, the non-animal derived soft capsule shell of present application shows improved disintegration stability and shell hardness by suppressing the increase of shell hardness caused by retrogradation of starch.

DESCRIPTION OF PRIOR ART

Conventionally, gelatin soft capsule has been manufactured by gelatin capsule shell and core components where at least one pharmaceutically active ingredients or functional ingredients have been solubilized or suspended. Further, gelatin capsule shell composition comprises gelatin as base material, purified water and other additives, such as glycerin, sorbitol. Further, coloring agent, flavoring agent, preservative and/or coating agent can be selectively added in gelatin capsule shell composition to enhance the quality and appearance.

Gelatin, a major component of capsule shell is an artificially made protein by partly hydrolysis of collagen derived from skin or bone tissue from animal, such as, bovine, pig or fish. However, vegetarian or some religious person avoids eating gelatin because gelatin has been made from animal origin material. Therefore, soft capsule shell made by non-animal origin material has been required according to the trend of vegetarian style. Accordingly, some hard or soft capsule derived from non-animal origin has been developed and marketed.

Many researches regarding soft capsule derived from non-animal origin have been carried out to make a soft capsule using starch derivatives and gums in accordance with consumption trend. In WO 2001/03677 A1 'Film forming compositions comprising modified starches and iota-carrageenan and methods for manufacturing soft capsules using same' by R. P. Scherer Technologies, Inc., non-animal derived film composition suitable for soft capsule comprising a mixture of iota-carrageenan and modified starch, plasticizer and disodium phosphate has been disclosed.

In this disclosure, said modified starch can be selected from hydroxypropylated tapioca starch, hydroxypropylated maize starch, acid thinned hydroxypropylated maize starch, potato starch and/or pregelatinized modified maize starches. Further, it has been disclosed that said modified starch has a hydration temperature below about 90° C. as well as a weight ratio of modified starch to iota-carrageenan in the range of 1.5:1~4.0:1 has to be required to produce a film composition suitable for soft capsule.

However, said film composition disclosed in this patent disclosure could not be commercialized due to its drawbacks, such as, integration delay of film or increase of shell hardness according to the retrogradation or gelatinization of starch.

Generally, the film composition for soft capsule having starch as main ingredient has been produced by starch or starch derivatives, gum, plasticizer, metal ion buffer and/or purified water. However, such film composition has a handicap that viscous starch solution becomes a micelle structure by being retrograded or rearranged when viscous starch solution is left for a long period.

In U.S. Pat. No. 6,214,376, a gelatin-free capsule composition comprising starch, water soluble plasticizer and kappa-carrageenan has been disclosed. Further, dispersible protein and/or potassium salt have been disclosed as another ingredient of capsule composition. On the other hand, in WO 2008/117682 A1 of PCT international publication, a capsule composition comprising ramda-carrageenan instead of kappa-carrageenan has been disclosed. Further, in this disclosure, a capsule composition has been manufactured by mixing starch, ramda-carrageenan, metal salt, dextrin, plasticizer and purified water.

In PCT International publication WO 2004/91530 A2 'Homogeneous, thermoreversible gel film containing kappa-2 carrageenan and soft capsules made therefrom', a homogeneous and thermoreversible gel film composition comprising kappa-2 carrageenan, optionally prasticizer, second film former, bulking agent and/or pH controlling agent has been disclosed. Further, it has been disclosed that starch, starch derivatives, starch hydrozylate, cellulose gum, kappa carrageenan, iota carrageenan, alginate, propylene glycol alginate, polymannan gum, dextrane, pectin, gellan, pullulan, alkylcellulose ether and/or modified alkylcellulose ether can be selected as second film former.

However, any soft capsule composition disclosed in above patent disclosure also could not solve the drawbacks of reduced disintegration according to the increase of shell hardness.

According to disintegration test requirement in Korean Pharmacopoeia 9th addition, soft capsule has to be disintegrated within 20 minutes. This Korean integration guideline is so tight compared to international integration guideline of soft capsule. Therefore, only a few non-animal derived soft capsules can satisfy Korean integration requirement.

Most of non-animal derived film composition for soft capsule have been manufactured by starch or starch derivatives, gum, plasticizer, metal ion buffer and/or purified water. As described above, starch can be easily retrograded by forming micelle structure after lapse of time.

On the other hand, starch can also be gelatinized by forming hydrogen bond associated with water molecules under room temperature after lapse of time. Such hydrogen bond can be formed either among 2 starch molecule and water molecule, or between hydroxyl groups in starch molecule. At the association point of starch molecule, starch molecules can be overlapped. Eventually, net structure of starch molecule may result in the delay of disintegration and increase of hardness.

To avoid the delay of disintegration and increase of hardness, the control of retrogradation of starch has been required. The selection of kind of starch is also important, because the degree of retrogradation can be varied according to the kinds of starch. Generally, maize, wheat or cereal starch tends to be easily retrograded, while potato, sweet potato or tapioca starch tends to be slowly retrograded. The preferred starch for soft capsule film can be waxy maize starch. Further, acid modified starch, hydroxypropylated modified starch or cross linked modified starch may be preferred rather than raw starch.

The inventor of present application has researched non-animal soft capsule shell composition for improving disintegration and suppressing shell hardness. In the course of researching the soft capsule shell composition, slow retrogradation starch has been selected, as well as antioxidant and/or disintegration enhancer has been employed to avoid the forming the net structure of starch molecule and/or forming the micelle structure. Finally, the inventor of present application has completed non-animal soft capsule shell composition having improved disintegration and shell hardness.

Problem to be Solved

The problem to be solved is to develop a soft capsule shell composition for improving disintegration and suppressing shell hardness. For solving the technical problem, slow retrogradation starch has been selected as base material. Further, antioxidant and/or disintegration agent has been employed to avoid the forming the net structure of starch molecule and/or forming the micelle.

Means for Solving the Problem

The object of present invention is to provide a non-animal derived soft capsule shell composition having improved disintegration and shell hardness comprising i) 15~30 wt % of at least one starch selected from raw starch, acid modified starch, hydroxypropylated modified starch, α-modified starch, cross-linked modified starch, starch hydrozylate and/or mixed starch of raw starch and modified starch; ii) 1.0~10 wt % of at least one gum selected from arabic gum, tragacanth gum, karaya gum, ghatti gum, guar gum, locust bean gum, tara gum, konjac, algin, agar, carrageenan, pullulan, pectin, gellan, mannan and/or xanthan gum; and iii) 1.0~20 wt % of plasticizer, 0.001~5 wt % of buffering agent, 0.001~3 wt % of disintegration agent, 0.001~2 wt % of antioxidant and a suitable amount of purified water.

Further, said non-animal derived soft capsule shell composition comprises 18~25 wt % of mixed starch containing hydroxypropylated tapioca starch/cross-linked potato starch/hydroxypropylated maize starch in the ratio of 1/0.1~0.5/0.1~0.3; 3~6 wt % of iota-carrageenan as gelling agent; 5~20 wt % of plasticizer; 0.01~3 wt % of buffering agent; 0.01~2 wt % of disintegration agent, 0.01~1 wt % of antioxidant and 45~60 wt % of purified water.

Further, the amount of said iota-carrageenan is in the range of 3.5~5.5 wt %.

On the other hand, said non-animal derived soft capsule shell composition comprises 18~25 wt % of hydroxypropylated tapioca starch; 2~4 wt % of iota-carrageenan and 0.5~1.5 wt % of kappa-carrageenan as gelling agent; 5~20 wt % of plasticizer; 0.01~3 wt % of buffering agent; 0.01~2 wt % of disintegration agent, 0.01~1 wt % of antioxidant and 45~60 wt % of purified water.

Further, the amount of said iota-carrageenan is in the range of 2.5~3.5 wt % and the amount of said kappa-carrageenan is in the range of 0.8~1.2 wt %.

Further, said plasticizer can be at least one selected from mannitol, crystalline or non-crystalline sorbitol, sorbitan, sucrose, xylitol, erythritol, maltitol, oligo sugar, iso-malto oligo sugar, glycerin, diglycerol or triglycerol.

Further, said buffering agent can be at least one selected from organo-metal salt, sodium phosphate dibasic or potassium phosphate dibasic.

Further, said disintegration agent can be at least one selected from glucoamylase, maltogenic amylase, alpha-amylase, beta-amylase, iso-amylase or pullulanase.

Further, said antioxidant can be at least one selected from rosemary extract, green tea extract, tocopherol or gallic acid.

Advantageous Effect

The outstanding advantageous effect of present application is to provide a soft capsule shell composition for improving disintegration and suppressing shell hardness. The soft capsule shell composition has adopted slow retrogradation starch as base material as well as antioxidant and disintegration agent to avoid the forming the net structure of starch molecule and/or forming the micelle. Further, the addition of antioxidant and disintegration agent to the starch base material can improve the disintegration of non-animal derived soft capsule by suppressing the increase of shell hardness resulted from retrogradation of starch.

PREFERRED EMBODIMENT OF INVENTION

The non-animal derived soft capsule shell composition having improved disintegration and shell hardness has adopted at least one starch selected from raw starch, acid modified starch, hydroxypropylated modified starch, α-modified starch, cross-linked modified starch, starch hydrozylate and/or mixed starch of raw starch and modified starch as base material. The amount of said starch base material is in the range of 15.0~30.0 wt % of total shell amount.

The gum used in soft capsule shell composition has a role of gelling agent of starch. Said gum can be at least one gum selected from arabic gum, tragacanth gum, karaya gum, ghatti gum, guar gum, locust bean gum, tara gum, konjac, algin, agar, carrageenan, pullulan, pectin, gellan, mannan and/or xanthan gum. The amount of said gum is in the range of 1.0~10.0 wt % of total shell amount.

Further, the non-animal derived soft capsule shell composition can also comprise plasticizer. Said plasticizer can be at least one selected from mannitol, crystalline or non-crystalline sorbitol, sorbitan, sucrose, xylitol, erythritol, maltitol, oligo sugar, iso-malto oligo sugar, glycerin, diglycerol or triglycerol. The amount of said plasticizer is in the range of 1.0~20.0 wt % of total shell amount.

Further, the non-animal derived soft capsule shell composition can also comprise buffering agent. Said buffering agent can be at least one selected from organo-metal salt, sodium phosphate dibasic or potassium phosphate dibasic. The amount of said buffering agent is in the range of 0.001~5.0 wt % of total shell amount.

On the other hand, the non-animal derived soft capsule shell composition can also comprise disintegration agent. Said disintegration agent can be at least one selected from glucoamylase, maltogenic amylase, alpha-amylase, beta-amylase, iso-amylase or pullulanase. The amount of said disintegration agent is in the range of 0.001~3.0 wt % of total shell amount. The preferred disintegration agent can be alpha-amylase, because it has thermal stability in the course of 85~95° C. heat treatment step during the manufacturing soft capsule film solution.

Further, the non-animal derived soft capsule shell composition can also comprise antioxidant. Said antioxidant can be at least one selected from rosemary extract, green tea extract, tocopherol or gallic acid. The amount of said antioxidant is in the range of 0.001~2.0 wt % of total shell amount. The preferred antioxidant can be gallic acid, which can delay the retrogradation of starch.

On the other hand, said non-animal derived soft capsule shell composition can also comprise a small amount of coloring agent, flavoring agent as well as a suitable amount of purified water. After forming the soft capsule film using said composition, core ingredient has been filled using rotary automatic filling machine.

Said core ingredient can be at least one of pharmaceutical active ingredient or functional food ingredient. Of course, any core ingredient can be used if it can be made by soluble or suspended form.

As one preferred embodiment of present application, following soft capsule shell composition can be explained.

As preferred embodiment, said non-animal derived soft capsule shell composition comprises 18~25 wt % of mixed starch containing hydroxypropylated tapioca starch/cross-linked potato starch/hydroxypropylated maize starch in the ratio of 1/0.1~0.5/0.1~0.3; 3~6 wt % of iota-carrageenan as gelling agent; 5~20 wt % of plasticizer; 0.01~3 wt % of buffering agent; 0.01~2 wt % of disintegration agent, 0.01~1 wt % of antioxidant and 45~60 wt % of purified water.

In preferred composition, tapioca starch has been selected due to it high amylopectin contents as well as good chewy texture having comparatively soft elasticity and viscosity. Further, tapioca starch can be easily absorbed into human body with low gelatinization temperature.

Hydroxypropylated modification of tapioca starch has been carried out in order to decline the gelatinization temperature of starch, improve the freezing resistance, delay the retrogradation and improve the chewy texture. Hydroxypropylated modification can be made by the reaction between starch and propylene oxide in the presence of alkali catalyst.

Therefore, hydroxypropylated tapioca starch has been made by treating tapioca starch with propylene oxide in the presence of alkali catalyst. Finally, the physical properties of origin tapioca starch have been modified through chemical treatment. However, such hydroxypropylated tapioca starch cannot have enough film strength, even though it has sufficient elasticity and viscosity for soft capsule film.

To optimize physical property of starch for soft capsule film, a mixed starch containing hydroxypropylated tapioca starch/cross-linked potato starch/hydroxypropylated maize starch in the ratio of 1/0.1~0.5/0.1~0.3 has been developed.

On the other hand, various kinds of gums as described above can be used as gelling agent of starch. As preferred embodiment, carrageenan, especially iota-carrageenan has been selected as gelling agent. The amount of iota-carrageenan is preferably in the range of 3.5~5.5 wt % of total shell composition.

As another preferred embodiment of present application, following soft capsule shell composition can be explained.

As preferred embodiment, said non-animal derived soft capsule shell composition comprises 18~25 wt % of hydroxypropylated tapioca starch; 2~4 wt % of iota-carrageenan and 0.5~1.5 wt % of kappa-carrageenan as gelling agent; 5~20 wt % of plasticizer; 0.01~3 wt % of buffering agent; 0.01~2 wt % of disintegration agent, 0.01~1 wt % of antioxidant and 45~60 wt % of purified water.

Hydroxypropylated tapioca starch has been adopted as base material, because hydroxypropylated tapioca starch has a good stability against retrogradation and/or gelatinization of starch. Other physical properties of hydroxypropylated tapioca starch can meet with the requirements for soft capsule film composition.

On the other hand, various kinds of gums as described above can be used as gelling agent of starch. As preferred embodiment, carrageenan can be selected as gelling agent. Further, a mixture of 2~4 wt % iota-carrageenan and 0.5~1.5 wt % kappa-carrageenan has been selected as gelling agent.

The amount of iota-carrageenan is preferably in the range of 2.5~3.5 wt %, whereas the amount of kappa-carrageenan is preferably in the range of 0.8~1.2 wt % of total shell composition.

For preparing the soft capsule film, a small amount of coloring agent, flavoring agent as well as a suitable amount of purified water have been added to above described composition. Using rotary automatic filling machine, core ingredient has been filled in the soft capsule shell.

The present application can be explained more concretely by following Preparation Examples and Examples. However, the scope of present application cannot be limited by following Examples.

PREPARATION1 EXAMPLE 1

Preparation of Soft Capsule Film Composition of Present Application

Non-animal derived soft capsule film composition of present application consists of amounts and ingredients as shown in Table 1.

TABLE 1

|  | per 100 kg solution |
| --- | --- |
| modified starch | 21.213 |
| polyglycerol | 9.449 |
| D-sorbitol solution | 9.449 |
| iota-carrageenan | 3.052 |
| kappa-carrageenan | 0.763 |
| sodium phosphate, dibasic | 0.763 |
| α-amylase | 0.020 |
| gallic acid | 0.100 |
| purified water | 55.191 |
| Total | 100.000 |

Preparation of Soft Capsule Film Composition of Present Application 100 kg of non-animal derived soft capsule film solution has been prepared by following method.

21.213 kg of modified starch, 9.449 kg of polyglycerol, 9.449 kg of D-sorbitol solution, 3.052 kg of iota-carrageenan, 0.763 kg of kappa-carrageenan, 0.763 kg of sodium phosphate, dibasic, 0.1 kg of gallic acid and 55.191 kg of purified water have been added and mixed in the melting tank. In the course of heating the mixture at 85~95° C. for 120 minutes, the mixture has been agitated in 40~45 rpm. After solubilizing the mixture, it has been laid under reduced pressure of 600~760 mmHg. Then, the solubilized mixture has been aged at 75~80° C. for 1~2 hours. Finally, non-animal derived soft film solution has been prepared. Before forming the soft capsule, 0.02 kg of α-amylase has been added and homogenized in the solution tank.

Forming the Non-Animal Derived Soft Capsule of Present Application

Borage seed oil has been employed as core ingredient. The soft capsule has been manufactured using Oval shape mold in the rotary automatic filling machine. The total weight of soft capsule filled with Borage seed oil is 500 mg including 250 mg of shell weight. Then, prepared soft capsule has been dried in tumbler for 16~20 hours as well as dried in tray. Finally, the sample has been prepared for stability test.

PREPARATION EXAMPLE 2

Preparation of Soft Capsule Film Composition of Present Application

Non-animal derived soft capsule film composition of present application consists of amounts and ingredients as shown in Table 2. 100 kg of non-animal derived soft capsule film solution has been prepared by following method. The total weight of soft capsule filled with Borage seed oil is 500 mg including 250 mg of shell weight.

HP tapioca starch, cross-linked potato starch, HP maize starch, glycerin, D-sorbitol solution, iota-carrageenan, sodium phosphate dibasic, gallic acid and purified water have been added and mixed in the melting tank. In the course of heating the mixture at 85~95° C. for 120 minutes, the mixture has been agitated in 40~45 rpm. After solubilizing the mixture, it has been laid under reduced pressure of 600~760 mmHg. Then, the solubilized mixture has been aged at 75~80° C. for 1~2 hours. Finally, non-animal derived soft film solution has been prepared. Before forming the soft capsule, 0.02 kg of α-amylase has been added and homogenized in the solution tank.

PREPARATION EXAMPLE 3

Preparation of Soft Capsule Film Composition of Present Application

Non-animal derived soft capsule film composition of present application consists of amounts and ingredients as shown in Table 2. 100 kg of non-animal derived soft capsule film solution has been prepared by following method. The total weight of soft capsule filled with Borage seed oil is 500 mg including 250 mg of shell weight.

HP tapioca starch, glycerin, D-sorbitol solution, iota-carrageenan, kappa-carrageenan, sodium phosphate dibasic, gallic acid and purified water have been added and mixed in the melting tank. In the course of heating the mixture at 85~95° C. for 120 minutes, the mixture has been agitated in 40~45 rpm. After solubilizing the mixture, it has been laid under reduced pressure of 600~760 mmHg. Then, the solubilized mixture has been aged at 75~80° C. for 1~2 hours. Finally, non-animal derived soft film solution has been prepared. Before forming the soft capsule, 0.02 kg of α-amylase has been added and homogenized in the solution tank.

Borage seed oil has been employed as core ingredient. The soft capsule has been manufactured using Oval shape mold in the rotary automatic filling machine. The total weight of soft capsule filled with Borage seed oil is 500 mg including 250 mg of shell weight. Then, prepared soft capsule has been dried in tumbler for 16~20 hours as well as dried in tray. Finally, the sample has been prepared for stability test.

TABLE 2

|  | per 100 kg solution | |
| --- | --- | --- |
|  | Preparation Example 2 | Preparation Example 3 |
| HP tapioca starch | 14.0 | 22.0 |
| cross-linked potato starch | 6.0 | — |
| HP maize starch | 2.5 | — |
| iota-carrageenan | 4.0 | 3.0 |
| kappa-carrageenan | — | 1.0 |
| glycerin | 8.5 | 8.5 |
| D-sorbitol solution | 8.0 | 8.0 |
| sodium phosphate, dibasic | 0.7 | 0.7 |
| α-amylase | 0.1 | 0.1 |
| coloring agent, flavoring agent and antioxidant | 0.8 | 0.8 |
| purified water | 55.4 | 55.9 |
| Total | 100.0 | 100.0 |

COMPARATIVE PREPARATION EXAMPLE 1

Preparation of Soft Capsule Film Composition Excluding Disintegration Agent and Antioxidant Soft capsule film composition in Comparative Preparation Example 1 has been made as the same manner of Preparation Example 1 except that disintegration agent and antioxidant have not been included in the composition.

The soft capsule film composition of Comparative Preparation Example 1 has not included antioxidant selected from rosemary extract, green tea extract, tocopherol or gallic acid as well as disintegration agent selected from glucoamylase, maltogenic amylase, alpha-amylase, beta-amylase, iso-amylase or pullulanase.

The soft capsule film composition of Comparative Preparation Example 1 consists of the amounts and ingredients as shown in Table 3.

TABLE 3

|  | weight per 100 kg solution |
| --- | --- |
| modified starch | 21.213 |
| glycerin | 9.449 |
| D-sorbitol solution | 9.449 |
| iota-carrageenan | 3.052 |
| kappa-carrageenan | 0.763 |
| sodium phosphate, dibasic | 0.763 |
| purified water | 55.311 |
| Total | 100.000 |

COMPARATIVE PREPARATION EXAMPLE 2

Preparation of Soft Capsule Film Composition by Changing the Amount of Starch

Soft capsule film composition in Comparative Preparation Example 2 has been made as the same manner of Preparation Example 1 by changing the amount of starch. The soft capsule film composition of Comparative Preparation Example 2 consists of the amounts and ingredients as shown in Table 4.

COMPARATIVE PREPARATION EXAMPLE 3

Preparation of Soft Capsule Film Composition by Changing the Amount of Starch

Soft capsule film composition in Comparative Preparation Example 3 has been made as the same manner of Preparation Example 1 by changing the amount of starch. The soft capsule film composition of Comparative Preparation Example 3 consists of the amounts and ingredients as shown in Table 4.

TABLE 4

|  | weight per 100 kg solution | |
|---|---|---|
|  | Preparation Example 2 | Preparation Example 3 |
| HP tapioca starch | 8.0 | 14.0 |
| cross-linked potato starch | 4.0 | — |
| HP maize starch | 2.5 | — |
| iota-carrageenan | 4.0 | 3.0 |
| kappa-carrageenan | — | 1.0 |
| glycerin | 8.5 | 8.5 |
| D-sorbitol solution | 8.0 | 8.0 |
| sodium phosphate, dibasic | 0.7 | 0.7 |
| α-amylase | 0.1 | 0.1 |
| coloring agent, flavoring agent and antioxidant | 30.8 | 0.8 |
| purified water | 63.4 | 63.9 |
| Total | 100.0 | 100.0 |

Samples have been prepared according to the methods disclosed in Preparation Examples and Comparative Preparation Examples.

EXAMPLE 1

Storage Stability and Disintegration Stability Test

The storage stability test including appearance test and leakage test has been carried out using the samples prepared according to the methods disclosed in Preparation Examples 1~3 and Comparative Preparation Examples 1~3. The storage stability test has been made after lapse of time under the storage conditions either 25° C., 60% (RH) for 24 months, or 40° C. 75% (RH) for 6 months. The samples have been inserted and sealed in HDPE bottle for storage stability test. Table 5 shows the results of storage stability test including appearance test and leakage test after lapse of time, 1 month, 3 months, and 6 months respectively.

TABLE 5

| Lapse of Time | Item | Prep. Ex. 1 | Prep. Ex. 2 | Prep. Ex. 3 | Comp. Prep. Ex. 1 | Comp. Prep. Ex. 2 | Comp. Prep. Ex. 3 |
|---|---|---|---|---|---|---|---|
| 1 month | Leakage | 0 | 0 | 0 | 0 | 0 | 0 |
|  | appearance | good | good | good | good | good | good |
| 3 months | Leakage | 0 | 0 | 0 | 0 | 0 | 0 |
|  | appearance | good | good | good | good | good | good |
| 6 months | leakage | 0 | 0 | 0 | 0 | 0 | 1 |
|  | appearance | good | good | good | good | good | good |

※ The number of leakage capsule has been measured using 100 capsules.

Disintegration stability test has been carried out according to the disintegration test protocol prescribed in Functional Food Guideline. In this test protocol, soft capsules are disintegrated with water by up-and-down movement for 20 minutes. The opening time means the time required for opening the soft capsule in the water, while completion time means the time required for complete disintegration of soft capsule in the water. Table 6 shows the results of integration stability test after lapse of time, 1 month, 3 months, and 6 months respectively.

TABLE 6

| Lapse of Time | Item | Prep. Ex. 1 | Prep. Ex. 2 | Prep. Ex. 3 | Comp. Prep. Ex. 1 | Comp. Prep. Ex. 2 | Comp. Prep. Ex. 3 |
|---|---|---|---|---|---|---|---|
| 1 month | Opening | 1 min. | 1 min. | 1 min. | 2 min. | 2 min. | 1.5 min. |
|  | Completion | 11 min. | 11 min. | 11 min. | 15 min. | 14 min. | 15 min. |
| 3 months | Opening | 2 min. | 2 min. | 1 min. 50 s | 3 min. | 3.5 min. | 2.5 min. |
|  | Completion | 13 min. | 13 min. | 13 min. | 20 min. | 22 min. | 17 min. |
| 6 months | Opening | 3 min. | 3 min. | 3 min. | 7 min. | 8 min. | 5 min. |
|  | Completion | 13 min. | 11 min. | 7 min. | insoluble | 25 min. | 20 min. |

As shown in Table 6, the samples prepared according to Preparation Examples 1~3 can meet with disintegration requirement after lapse of time for 6 months under accelerated condition (40° C., 75% (RH)), while the sample prepared according to Comparative Preparation Example 1 cannot meet with disintegration requirement after lapse of time for 6 months under accelerated condition. Therefore, the soft capsule film composition of present application shows better disintegration stability compared to conventional soft capsule film composition made by starch.

EXAMPLE 2

Hardness and Brittle Test of Soft Capsule

Hardness test has been carried out after lapse of time, 1 month to 24 months under normal condition (25° C., 60% (RH)) regarding soft capsule samples prepared according to Preparation Examples 1~3 and Comparative Preparation Examples 1~3.

Hardness has been measured by pressing the sample with a certain force for 20 seconds using ERWEKA TBH 225 TD Hardness Meter. The pressing force has been measured under the unit of Newton (N). Table 7 shows the results of hardness of samples after lapse of time 1, 3, 6, 12, 18, 24 months respectively under normal condition (25° C., 60% (RH)).

TABLE 7

| Lapse of Time | Prep. Ex. 1 | Prep. Ex. 2 | Prep. Ex. 3 | Comp. Prep. Ex. 1 | Comp. Prep. Ex. 2 | Comp. Prep. Ex. 3 |
| --- | --- | --- | --- | --- | --- | --- |
| 1 month | 5 N | 5 N | 5 N | 5 N | 5 N | 5 N |
| 3 months | 5 N | 5 N | 5 N | 5 N | 5 N | 5 N |
| 6 months | 5 N | 5 N | 5 N | 5 N | 5 N | 5 N |
| 12 months | 5 N | 5 N | 5 N | 5 N | 5 N | 5 N |
| 18 months | 5 N | 5 N | 6 N | 5 N | 5 N | 6 N |
| 24 months | 5 N | 5 N | 7 N | 6 N | 6 N | 6 N |

Hardness test has been carried out after lapse of time, 1 month to 24 months under cooled condition (4° C.) regarding soft capsule samples prepared according to Preparation Examples 1~3 and Comparative Preparation Examples 1~3. Hardness has been measured by pressing the sample with a certain force for 20 seconds using ERWEKA TBH 225 TD Hardness Meter. The pressing force has been measured under the unit of Newton (N). Table 8 shows the results of hardness of samples after lapse of time 1, 3, 6, 12, 18, 24 months respectively under cooled condition (4° C.).

TABLE 8

| Lapse of Time | Prep. Ex. 1 | Prep. Ex. 2 | Prep. Ex. 3 | Comp. Prep. Ex. 1 | Comp. Prep. Ex. 2 | Comp. Prep. Ex. 3 |
| --- | --- | --- | --- | --- | --- | --- |
| 1 month | 6 N | 6 N | 6 N | 6 N | 6 N | 6 N |
| 3 months | 6 N | 6 N | 6 N | 6 N | 6 N | 6 N |
| 6 months | 6 N | 7 N | 7 N | 7 N | 7 N | 7 N |
| 12 months | 7 N | 7 N | 7 N | 8 N | 7 N | 8 N |
| 18 months | 7 N | 7 N | 7 N | 8 N | 8 N | 9 N |
| 24 months | 7 N | 7 N | 7 N | 9 N | 9 N | 9 N |

As shown in Tables 7 and 8, the hardness of soft capsule samples prepared according to Preparation Examples 1~3 seldom increases after a lapse of time under both normal condition and cooled condition. However, the hardness of soft capsule sample prepared according to Comparative Preparation Example 1 increases into 7N after lapse of 24 months under normal condition as well as into 9N after lapse of 24 months under cooled condition. Other samples prepared according to Comparative Preparation Examples 2~3 show the similar increase of hardness as Comparative Preparation Example 1.

Brittle test has been carried out by dropping 30 g of plastic clapper from 30 cm of height in the drum. The brittle of soft capsule sample has been measured after lapse of time under normal condition (25° C., 60% (RH)). Table 9 shows the results of brittle of samples after lapse of time 1, 3, 6, 12, 18, 24 months respectively.

TABLE 9

| Lapse of Time | Prep. Ex. 1 | Prep. Ex. 2 | Prep. Ex. 3 | Comp. Prep. Ex. 1 | Comp. Prep. Ex. 2 | Comp. Prep. Ex. 3 |
| --- | --- | --- | --- | --- | --- | --- |
| 1 month | X | X | X | X | X | X |
| 3 months | X | X | X | X | X | X |
| 6 months | X | X | X | X | X | X |
| 12 months | X | X | X | X | X | X |
| 18 months | X | X | X | ○ | X | X |
| 24 months | X | X | X | ○ | ○ | ○ |

The brittle of soft capsule sample has been measured after lapse of time under cooled condition (4° C.). Table 10 shows the results of brittle of samples after lapse of time 1, 3, 6, 12, 18, 24 months respectively under cooled condition (4° C.).

TABLE 10

| Lapse of Time | Prep. Ex. 1 | Prep. Ex. 2 | Prep. Ex. 3 | Comp. Prep. Ex. 1 | Comp. Prep. Ex. 2 | Comp. Prep. Ex. 3 |
| --- | --- | --- | --- | --- | --- | --- |
| 1 month | X | X | X | X | X | X |
| 3 months | X | X | X | X | X | X |
| 6 months | X | X | X | X | X | X |
| 12 months | X | X | X | ○ | X | X |
| 18 months | X | X | X | ○ | ○ | ○ |
| 24 months | X | X | X | ○ | ○ | ○ |

As shown in Tables 9 and 10, the brittle of soft capsule samples prepared according to Preparation Examples 1~3 has not occurred after a lapse of time under both normal condition and cooled condition. However, the brittle of soft capsule sample prepared according to Comparative Preparation Example 1 has occurred after lapse of 18 months under normal condition as well as 12 months under cooled condition. Other samples prepared according to Comparative Preparation Examples 2~3 show the similar occurrence of brittle same as Comparative Preparation Example 1. Therefore, the soft capsule samples of present application show the improved stabilities in both hardness and brittleness.

The invention claimed is:

1. A non-animal derived soft capsule shell composition having improved disintegration and shell hardness comprising:
   i) 18 to about 25 wt % of mixed starch containing hydroxypropylated tapioca starch/cross-linked potato starch/hydroxypropylated maize starch in the ratio of 1/0.1 to about 0.5/0.1 to about 0.3;
   ii) 3 to about 6 wt % of iota-carrageenan as gelling agent;
   iii) 5 to about 20 wt % of plasticizer;
   iv) 0.01 to about 3 wt % of buffering agent;
   v) 0.01 to about 2 wt % of disintegration agent at least one selected from glucoamylase, maltogenic amylase, alpha-amylase, beta-amylase, iso-amylase or pullulanase;

vi) 0.01 to about 1 wt % of antioxidant; and
vii) 45 to about 60 wt % of purified water.

2. The non-animal derived soft capsule shell composition according to claim 1, wherein the amount of said iota-carrageenan is in the range of 3.5 to about 5.5 wt %.

3. The non-animal derived soft capsule shell composition according to claim 1, wherein said non-animal derived soft capsule shell composition comprises 2 to about 4 wt % of iota-carrageenan and 0.5 to about 1.5 wt % of kappa-carrageenan as gelling agent; 5 to about 20 wt % of plasticizer; 0.01 to about 3 wt % of buffering agent; 0.01 to about 2 wt % of disintegration agent; 0.01 to about 1 wt % of antioxidant and 45 to about 60 wt % of purified water.

4. The non-animal derived soft capsule shell composition according to claim 3, wherein the amount of said iota-carrageenan is in the range of 2.5 to about 3.5 wt % and the amount of said kappa-carrageenan is in the range of 0.8 to about 1.2 wt %.

5. The non-animal derived soft capsule shell composition according to claim 1, wherein said plasticizer is at least one selected from mannitol, crystalline or non-crystalline sorbitol, sorbitan, sucrose, xylitol, erythritol, maltitol, oligo sugar, iso-malto oligo sugar, glycerin, diglycerol or triglycerol.

6. The non-animal derived soft capsule shell composition according to claim 1, wherein said buffering agent is at least one selected from organo-metal salt, sodium phosphate dibasic or potassium phosphate dibasic.

7. The non-animal derived soft capsule shell composition according to claim 1, wherein said antioxidant is at least one selected from rosemary extract, green tea extract, tocopherol or gallic acid.

* * * * *